(12) United States Patent
Lohmeier et al.

(10) Patent No.: US 9,731,415 B2
(45) Date of Patent: Aug. 15, 2017

(54) METHOD FOR THE ALIGNMENT OF A MULTIAXIAL MANIPULATOR WITH AN INPUT DEVICE

(71) Applicant: KUKA Roboter GmbH, Augsburg (DE)

(72) Inventors: Sebastian Lohmeier, Munich (DE); Cyrill Von Tiesenhausen, Augsburg (DE)

(73) Assignee: KUKA Roboter GmbH, Augsburg (DE)

( * ) Notice: Subject to any disclaimer, the term of this patent is extended or adjusted under 35 U.S.C. 154(b) by 0 days.

(21) Appl. No.: 14/964,282

(22) Filed: Dec. 9, 2015

(65) Prior Publication Data
US 2016/0199984 A1 Jul. 14, 2016

(30) Foreign Application Priority Data
Jan. 14, 2015 (DE) .................. 10 2015 200 428

(51) Int. Cl.
| | | |
|---|---|---|
| *A61B 34/20* | (2016.01) | |
| *B25J 3/04* | (2006.01) | |
| *A61B 34/30* | (2016.01) | |
| *A61B 1/00* | (2006.01) | |
| *B25J 9/16* | (2006.01) | |

(Continued)

(52) U.S. Cl.
CPC ............ *B25J 3/04* (2013.01); *A61B 1/00149* (2013.01); *A61B 34/20* (2016.02); *A61B 34/30* (2016.02); *A61B 34/74* (2016.02); *B25J 9/1607* (2013.01); *B25J 9/1625* (2013.01); *B25J 13/00* (2013.01); *B25J 13/02* (2013.01); *B25J 13/025* (2013.01);
(Continued)

(58) Field of Classification Search
CPC ......... G05B 19/423; G05B 2219/39398; B25J 9/1692
See application file for complete search history.

(56) References Cited

U.S. PATENT DOCUMENTS 5,021,969 A * 6/1991 Okamura ............. G05B 19/427
700/261
6,124,693 A * 9/2000 Okanda ............... G05B 19/4086
318/564

(Continued)

FOREIGN PATENT DOCUMENTS

| | | |
|---|---|---|
| DE | 3223896 | 1/1984 |
| DE | 10 2004 020 09 A1 | 11/2005 |
| JP | 2014-129782 | 4/2004 |

OTHER PUBLICATIONS

The extended European Search Report, mailed on Jun. 10, 2016, in the related European Patent Appl. No. 15202003.8.

(Continued)

*Primary Examiner* — Dale Moyer

(57) ABSTRACT

A method is provided for the alignment of a multiaxial manipulator with an input device, which serves to control the manipulator, which method includes the steps of execution of one or more reference movements with the input device, execution of one or more reference movements with the manipulator, recording of the executed reference movements, calculation of a transformation matrix based on the recorded reference movements, and use of the calculated transformation matrix for the alignment of the movements of the input device with the manipulator.

20 Claims, 1 Drawing Sheet

(51) Int. Cl.
*B25J 13/00* (2006.01)
*B25J 13/02* (2006.01)
*B25J 13/08* (2006.01)
*A61B 34/00* (2016.01)
*A61B 34/35* (2016.01)
*A61B 17/00* (2006.01)

(52) U.S. Cl.
CPC ... *B25J 13/084* (2013.01); *A61B 2017/00207* (2013.01); *A61B 2034/301* (2016.02)

(56) References Cited

U.S. PATENT DOCUMENTS

| | | | |
|---|---|---|---|
| 6,364,888 B1 | 4/2002 | Niemeyer et al. | |
| 8,918,207 B2 | 12/2014 | Prisco | |
| 2005/0027394 A1* | 2/2005 | Graf | B25J 9/1682 700/245 |
| 2005/0240309 A1 | 10/2005 | Bischoff | |
| 2006/0074527 A1* | 4/2006 | Bhatt | B25J 9/1658 700/251 |
| 2007/0283970 A1* | 12/2007 | Mohr | A61B 34/70 128/898 |
| 2009/0132088 A1 | 5/2009 | Taitler | |
| 2010/0145520 A1* | 6/2010 | Gerio | B25J 13/06 700/264 |
| 2010/0312391 A1* | 12/2010 | Choi | B25J 9/1656 700/254 |
| 2010/0332031 A1* | 12/2010 | Itkowitz | B25J 9/1689 700/245 |
| 2011/0118753 A1 | 5/2011 | Itkowitz et al. | |
| 2012/0143353 A1 | 6/2012 | Kishi | |
| 2013/0338830 A1* | 12/2013 | Roethling | G05B 19/423 700/257 |
| 2014/0160015 A1* | 6/2014 | Ogawa | B25J 13/02 345/156 |
| 2014/0277740 A1 | 9/2014 | Adelman | |
| 2016/0052128 A1* | 2/2016 | Zimmermann | B25J 9/0081 700/261 |

OTHER PUBLICATIONS

The English translation of the Chinese Office Action, mailed on Oct. 10, 2016, in the related Chinese Patent Appl. No. 201610022435.5.
Examination Report from GPTO in DE Appl. No. 102015200428.7, dated Aug. 3, 2015.
Response to the Examination Report from GPTO in DE Appl. No. 102015200428.7, filed on Nov. 18, 2015.
The English translation of the Korean Office Action, mailed on Jan. 21, 2016, in the related Korean Appl. No. 2016-0003022.

* cited by examiner

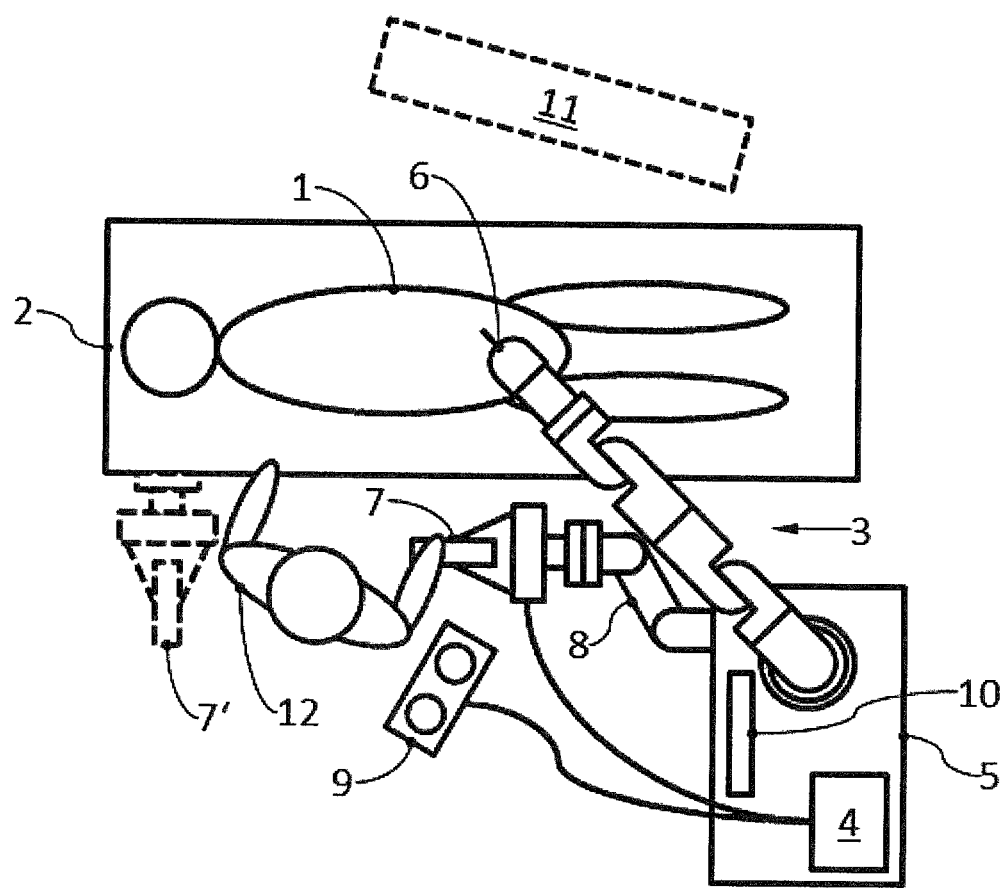

METHOD FOR THE ALIGNMENT OF A MULTIAXIAL MANIPULATOR WITH AN INPUT DEVICE

This application claims the benefit of priority under 35 §119(a) to German Patent Application No. 10 2015 200 428.7, filed on Jan. 14, 2015.

1. TECHNICAL FIELD

The present invention generally relates to a method for the alignment of a multiaxial manipulator with an input device and, in particular, a simplified alignment of the reference coordinate system of an input device with the coordinate system of a manipulator to be operated therewith.

2. TECHNICAL BACKGROUND

Manipulators, such as jointed-arm robots, in particular, are used for various work processes in, for example, assembly or production in the industrial environment. In addition, manipulators have applications in the field of medicine, in particular in the surgical field, for the performance of and assistance in operations, in particular in activities, which require a particularly precise manipulation of tools.

Manipulators can be mobile or employed at a fixed location. The manipulator is preferably a three-dimensional mobile jointed-arm robot, which is made up of several pivot joints and/or sliding joints. The pivot joints or sliding joints are usually connected to arm links, and every pivot joint or sliding joint is assigned a joint axis. A robot system comprises one or more manipulators, a control device and an input device. Robot systems are already known in surgery or interventional radiology, wherein the input devices are fixed to a control console. The relative alignment of the input devices is set and cannot be changed. This makes usage by the doctor difficult, as it negatively affects the freedom of movement and access to the patient.

In addition, systems are known in which a flexible catheter is pushed forwards and controlled by a robot. The input device is spatially separated from the robot in this system. The alignment of the input device is, in each case, relative to the top of the instrument, with the instrument being mounted at the end of the robot arm.

Finally, robot systems are known, in which input devices are installed spatially separated from the workplace of the manipulator, so-called telemanipulation systems. The input devices are fixed to a control console, with the alignment of the input devices being relative to a screen-presented and camera-supported, e.g. endoscopic, image display, the alignment of which relative to the manipulator or the manipulators of the robot system is set.

A common feature of all of the above-mentioned systems is that the input device is spatially separated from the manipulator, or the alignment of the input device relative to the manipulator to be operated is preset. This has the disadvantage that the alignment of the input devices during use, e.g. in an operation, cannot be easily changed. Although changing the position of the input device is conceivable, this would, however, also change the position of the input device relative to the manipulator, which would mean that the control of the robot system could no longer be realized intuitively. For example, the input devices are usually aligned with the manipulator to be operated such that a forwards movement, for example, of a joystick leads to a corresponding forwards movement of the manipulator in the same direction. If the input device is pivoted by, for example, 90°, this coupling, which is intuitively simple for the user, is no longer available.

Another disadvantage of the above-mentioned systems is that a simultaneous use of manual instruments or tools and robotically guided instruments or tools is not possible or is only possible with great difficulty, as the input device, for example, is not in the vicinity of the workplace of the manipulator, in particular an operating table, or the orientation of the input device cannot be adapted to the installation location.

In addition, the above-mentioned systems have the disadvantage that they offer no mode for gravity compensation or for sensitive manual guidance.

In view of the above-explained systems, the objective of the present invention is to provide a method and a system which allow simple alignment of a multiaxial manipulator with an input device. This allows the user of the robot system, in particular during a work process, e.g. an operation, to intraoperatively change the position or orientation of the input device, without having to sacrifice a control that is as intuitive as possible.

These and other objectives are achieved by means of the subject matter of the main claims.

3. CONTENT OF THE INVENTION

The present invention comprises a method for the alignment of a multiaxial manipulator with a corresponding input device and, in particular, an alignment of the reference coordinate system of an input device fixed onto an object with the coordinate system of a manipulator to be operated therewith, in particular the tool coordinate system. The multiaxial manipulator is preferably a jointed-arm robot. The input device serves to control the manipulator. An alignment of input device and manipulator is required and advantageous, for example, when the user changes the position or orientation of the input device, in order to obtain, for example, better access to the workspace of the manipulator, for instance, better access to a patient in a robot-assisted operation. This (re)alignment of input device and manipulator allows the operation to be adjusted to the requirements of the user. This advantageously permits a simpler and more intuitive operation of the manipulator.

In the method according to the invention, one or more reference movements are executed with the input device. The input device (for example, a space controller or touch-sensitive surfaces, such as touchpads or touchpad monitors, for example) is moved in specific directions, in order to recalibrate, for example, the X and Y alignment of the input device.

In a further step, one or more corresponding reference movements are executed with the manipulator, for example, by means of a direct guiding of the manipulator by hand. The manipulator is moved in specific directions and preferably in such a way that the corresponding reference movements of the manipulator correspond to the reference movements carried out with the input device. The user thus preferably executes the reference movements of the manipulator in such a way that he/she obtains a desired alignment of manipulator and input device. The user preferably defines the reference coordinate systems (R-COS) of manipulator and input device, by executing corresponding reference movements with manipulator and input device. The reference movements are recorded by the robot controller.

The reference movements executed by the user are preferably suitable for calculating an alignment of the two reference coordinate systems. For applications which do not require an absolute positioning of, for example, the tool, it is sufficient to define only the orientation of the two reference coordinate systems. A definition of the coordinate origin (COO) is not absolutely necessary in this case.

By means of the optional specification of a coordinate origin, it is possible to fully define a reference coordinate system. A full definition can be advantageous in conjunction with imaging methods, in order to display patient images or patient models in the workspace of the manipulator, for example.

A reference coordinate system (and optionally a coordinate origin) can preferably be defined using the following inputs:

a) by means of three points, with one of these points optionally being able to be defined as coordinate origin;
b) by means of two axes, with a coordinate origin additionally being able to be optionally preset, by means of:
  i. movements along two substantially orthogonal straight lines, which can otherwise have any alignment in space whatsoever;
  ii. a substantially L-shaped movement, i.e. a curved line produced by two orthogonal sections;
  iii. two surface axes, with, from two circular movements, the axes orthogonal to the movement being identified in each case, with the surface axes alternatively also being able to be determined by means of two pivots executed with the manipulator or the input device; or
  iv. one point and two directions or two points and two directions;
c) Generation of a plane, with a coordinate origin additionally being able to be optionally preset, by means of
  i. a substantially L-shaped movement
  ii. a substantially circular movement; or
  iii. a general, substantially planar movement.

The executed reference movements are recorded, for example, by a control device, i.e. both the reference movements executed with the input device and also the reference movements executed with the manipulator are recorded. It is preferably the control device of the manipulator that records the executed reference movements.

The movements are preferably respectively recorded using position sensors integrated into the manipulator or input device and are preferably transmitted for further processing to the control device, and there they are stored at least temporarily for further processing. The recording of the movements can also, however, be carried out by an external navigation system located around the workspace of the manipulator and input device. Marks to be recorded, for example, are applied to the manipulator or to the input device and are recorded by the external navigation system, for example, optically.

In a further step, a transformation matrix is calculated based on the recorded reference movements. The transformation matrix contains values calculated on the basis of the reference movements, which are used for the alignment of the coordinate system of the input device with the coordinate system of the manipulator. The coordinate systems of the input device and the manipulator or of the tool, which is mounted on the manipulator, are aligned with one another. The transformation matrix is preferably calculated on the basis of one or more algorithms, which are stored in the control device.

Following calculation of the transformation matrix, the user preferably receives a response from the control device, e.g. visually on a monitor, or audibly.

In a further step, the calculated transformation matrix is used for the alignment of the movements of the input device with the manipulator. To do this, the movements of the input device are preferably modelled, with the help of the transformation matrix, onto the manipulator. After the alignment, the manipulator can once again be controlled intuitively via the input device.

The invention offers the advantage of an improved, more intuitive and more flexible operation of the manipulator. In addition, the method allows the user to easily align the reference coordinate system of an input device with the (tool) coordinate system of a manipulator and thus allows realization of a flexible and quick user-dependent adjustment of the manipulator.

Preferably, between the steps of the recording of the reference movements and the calculation of the transformation matrix, a compensating geometry for the recorded reference movements is calculated by means of a control device. To do this, for the points of the reference movements recorded in a total point cloud, corresponding partial point clouds for the individual straight lines and/or planes are identified and stored. Subsequently, straight lines or planes are fitted into the partial point clouds. This generally takes place using a compensating calculation, usually in accordance with the least squares method. The compensating geometry is, by way of example, a straight line, which is calculated on the basis of the (not necessarily straight) reference movement. A calculation of a compensating geometry can be required, because the user-executed reference movements of the manipulator, for example, typically exhibit deviations from a theoretical ideal geometry, for example, if the user, when executing the reference movement of the manipulator, directly guides this manipulator by hand.

In addition, after calculation of the compensating geometry, a plausibility check is preferably realized on the basis of compensating geometry data. This involves checking the data represented by the compensating geometries with regard to plausibility. In addition to the checking for completeness and consistency, the plausibility check can comprise, in particular, checks for orthogonality of the compensating geometries and/or straightness of the reference movements (line) or planarity of the reference movement (plane). For the assessment of the straightness of the reference movements (line) or planarity of the reference movement (plane), a quality measure can be used, which is based on a comparison of the (measured) partial point clouds with the (calculated) compensating geometries, for example, a mean or maximum deviation of a measuring point from the calculated geometry. For all the above-mentioned checking steps of the plausibility check, corresponding limit values are stored in the control device, which can optionally be defined in an application-specific manner.

In addition, the manipulator preferably has one or more axes with means for recording forces and/or torques. These means can comprise, for example, one or more sensors, which are preferably disposed in one or more joints of the manipulator. These one or more sensors can also be disposed, for example, on the end effector, the manipulator base, or at another location along the manipulator. The means for recording forces and/or torques can also be based on a measurement of current values, preferably in the drives of the manipulator. In one example, a multiaxial force/torque sensor can be provided on the end effector, without additional force/torque sensors being provided in the joints.

Preferably, means for detecting a user interaction, e.g. touch-sensitive sensors, can also be disposed on the manipulator.

In addition, the manipulator is preferably controlled on the basis of its tool coordinate system.

The step of the execution of one or more corresponding reference movements with the manipulator preferably comprises a direct guiding of the manipulator by hand. To do this, the manipulator is gripped or grasped by the user and then directly guided by hand, i.e. the manipulator is not indirectly guided by means of command keys or the like. The direct guiding of the manipulator by hand has the advantage that the user can easily grasp the manipulator and can move it according to his/her desire, so that the manipulator does exactly what the user specifies. This is in particular advantageous, as it means that the user can easily and without significant complications, for example, during a work process, align the input device with the manipulator, in an optimal and intuitive manner. This results in a reduction of workload for the user, since he/she is spared the trouble of laborious inputs into devices and the like in order to achieve optimal alignment of the input device, and no advanced technical knowledge about the functioning of the robot system is required. The method according to the invention is additionally suitable for being carried out with a manipulator with sensors disposed thereon, in particular integrated torque sensors, since these allow a direct guiding of the manipulator by hand in a simple manner. The step of execution of one or more corresponding reference movements with the manipulator thus preferably comprises the operation of the manipulator in an operating mode for active compliance control, in particular gravity compensation.

The manipulator is preferably equipped with one or more tools, such that these can be moved by the manipulator. In particular, these tools can be medical instruments, with the medical instruments comprising endoscopes, ultrasound probes, instruments for open or minimally invasive surgery, puncture needles or biopsy needles. In another embodiment, these tools can also be, in particular, industrially employed machining tools, e.g. for joining, bonding, welding, seaming, boring, screwing, etc.

The input device preferably comprises one of a haptic hand controller, joystick, 3D motion controller, capacitive touchpad, several switches for triggering special functions and/or pre-programmed movement sequences of the manipulator and/or of the tool, or non-contact sensors, such as a KINECT camera or LEAP MOTION device.

Preferably, the input device is mounted, for example, detachably, on a jointed supporting arm. This makes it possible to flexibly move the input device to a new position and, if necessary, to also release it from its current installation location and install it at another location. The joints of the supporting arm preferably have sensors for recording the joint positions of the supporting arm. This allows the control device to determine what position the input device is in at any point in time. These measurement values can then be used to identify the transformation matrix just once at the beginning of a work process in accordance with the above-described method according to the invention. In the event of a movement of the supporting arm out of the original position by the user, the transformation matrix is automatically updated in the control device on the basis of the measured position values. After successful updating of the transformation matrix, the user optionally receives a response from the control device (e.g. visually on a monitor, by means of an indicator light, and/or audibly).

The one or more reference movements of the input device and the corresponding one or more reference movements of the manipulator are preferably recorded simultaneously or sequentially. In order to record the reference movements, the control device is, for example, configured such that the user-executed reference movements of the manipulator and input device are simultaneously recorded. In the present case, this means that the user executes the required movements (one or more reference movements) at the same time with the manipulator and the input device. For example, the user executes with his/her left hand the movement with the manipulator and with his/her right hand the movement with the input device (or vice versa). Alternatively, it is possible for the user to execute all required movements one after the other (sequentially) with the manipulator and the input device with the same result. This means that the user firstly executes the movement with the input device and then with the manipulator (or vice versa).

In another example, it is possible for the user to initially execute all reference movements on either the input device or on the manipulator and then all corresponding reference movements on the respective other device (manipulator or input device), depending on whether the user began on the input device or manipulator.

In addition, one or more external operating elements, in particular, a foot-operated switch connected to the control device, are preferably configured to switch between operating modes or to trigger an action of the tool. These operating modes comprise, for example, an alignment mode, which can be activated to execute the alignment of the input device with the multiaxial manipulator.

An external monitor is preferably provided, which is configured to present camera images, e.g. endoscope images and/or pictures from an external imaging system and/or navigation system.

According to the invention, a robot system, in particular a modular robot system, is additionally provided, which comprises a control device, a manipulator and an input device. The control device is preferably configured to allow an alignment of the manipulator with the input device, in that it records executed reference movements of the input device and corresponding movements of the manipulator, calculates a transformation matrix based on the recorded reference movements, and uses the calculated transformation matrix for the alignment of the movements of the input device with the manipulator.

In addition, the invention provides for a use of an above-described method during an operation on a person or in an industrial process.

The (re)alignment of the manipulator with the input device can be initiated, for example, by selection of an alignment mode. This alignment mode can either be active immediately after the switching on or reset of the manipulator or the robot controller or can be activated by means of a user input or program sequence.

A reference movement executed by the user can preferably be used to determine a (fundamental) specification for a movement scaling between input device and manipulator. For this purpose, either the recorded reference movements can be used or separate movements can be recorded. The decisive factor for the scaling is, in both cases, the ratio of the movement spaces used for the reference movement of the input device and manipulator.

4. EXEMPLARY EMBODIMENT

The present invention is described in greater detail below with reference to the accompanying FIGURE. The method according to the invention is suitable, in particular, for use in a modular robot system, as depicted in FIG. 1.

A patient 1 lies on an examination or operating table 2. A manipulator 3 is integrated, together with a corresponding control device 4, into a mobile cart 5. A medical instrument 6 is mounted at the distal end of the manipulator 3 in such a way that it can be moved by the manipulator 3. In addition, an input device 7 is mounted on the cart 5, which input device is connected to the control device 4, such that a user can control the movement of the manipulator 3. The user can ergonomically align the input device 7 in his/her working environment by means of a jointed supporting arm 8. A display 10 is mounted rigidly or jointed on the cart, which can optionally be touch-sensitive (e.g. touchscreen), for the presentation of operating parameters and/or of the system status.

The robot system is placed on the table 2 by the medical personnel or the user in such a way that the intervention location or examination location on the patient 1 is reached with the medical instrument 6, while at the same time allowing a high level of manipulability of the manipulator 3, and with the patient 1 still being sufficiently accessible for the user 12 and, optionally, additional medical personnel. Before an intervention, an operation or an examination is performed, the input device 7 is aligned or moved by the user into a position which is comfortable for him/her with the help of the supporting arm 8. The input device 7 can optionally be detached from the supporting arm 8 and fixed to another object, for example, the table 2. This installation option is depicted in FIG. 1 by the input device 7'.

Since the input device was previously located in a specific alignment with the manipulator and the user has now moved the input device 7, e.g. with the help of the supporting arm 8, the user will now no longer necessarily be able to use the robot system intuitively, since the input device 7 and the manipulator 3 are no longer optimally aligned with one another. In order to align the input device 7 and the manipulator 3, the user initially operates a foot-operated switch 9 connected to the control device 4 in order to activate a mode for the alignment of the coordinate systems of the input device 7 and the manipulator 3 (alignment mode). This mode is either active immediately after the switching on or reset of the robot system or the control device or is activated by means of a user input or program sequence. This latter scenario occurs, for example, by means of operating element 10, monitor 11 (if it is touch-sensitive) or another operating element integrated into cart 5. By activation of the alignment mode, the manipulator 3 is operated in an operating mode for active compliance control, in particular, gravity compensation, so that the user 12 is able to move this manipulator freely.

The user initially executes a reference movement with the input device 7 and then a corresponding reference movement with the manipulator 3. Following execution of the reference movements, the control device 4 records these reference movements, calculates a transformation matrix therefrom, and uses this for the alignment of the input device 7 and the manipulator 3. The user has thus obtained in a very simple and intuitive way a (re)alignment of input device 7 and manipulator 3 which is optimal for him/her, which allows him/her an intuitive use of the robot system during the operation. The user is additionally able to simultaneously use the robot system and a manually operated instrument, as the user is located alongside the robot system at the patient's side.

It should be noted that the invention claimed herein is not limited to the described embodiments, but may be otherwise variously embodied within the scope of the claims listed infra.

The invention claimed is:

1. A method for the alignment of a multiaxial manipulator with an input device fixed onto an object, which input device serves to intuitively control the manipulator, comprising:
   a) executing one or more reference movements with the input device, the one or more reference movements defining a reference coordinate system of the input device;
   b) executing one or more corresponding reference movements with the manipulator by means of a direct guiding of the manipulator by hand, the one or more reference movements defining a reference coordinate system of the manipulator;
   c) recording the executed reference movements of the input device and the manipulator;
   d) calculating a transformation matrix based on the recorded reference movements of the input device and the manipulator; and
   e) using the calculated transformation matrix for the alignment of subsequent movements of the input device with corresponding movements of the manipulator.

2. The method according to claim 1, wherein, between steps c) and d), a compensating geometry for the recorded reference movements is calculated by means of a control device; and
   wherein, after calculation of the compensating geometry, a plausibility check is realized on the basis of compensating geometry data.

3. The method according to claim 1, wherein the manipulator has one or more axes with sensors for recording forces and torques.

4. The method according to claim 1, wherein the manipulator has one or more axes with sensors for detecting a user interaction.

5. The method according to claim 1, wherein the manipulator has a tool coordinate system and is controlled on the basis of its tool coordinate system.

6. The method according to claim 1, wherein the step of executing the one or more corresponding reference movements with the manipulator by means of a direct guiding of the manipulator by hand and comprises operating the manipulator in an operating mode for active compliance control.

7. The method according to claim 1, wherein the manipulator is equipped with at least one tool.

8. The method according to claim 7, wherein the at least one tool is an industrially employed machining tool for joining, bonding, welding, seaming, boring or screwing.

9. The method according to claim 1, wherein the input device is selected from the group consisting of haptic hand controllers, joysticks, 3D motion controllers, capacitive touchpads, switches configured for one or more of triggering special functions or pre-programmed movement sequences of the manipulator, and non-contact sensors.

10. The method according to claim 1, wherein the input device is mounted on a jointed supporting arm; and
   wherein the joints of the supporting arm have sensors for recording joint positions of the supporting arm.

11. The method according to claim 1, wherein the input device is mounted on a jointed supporting arm; and
   wherein at least one of the location of the supporting arm or the location of the input device is recorded with an external navigation system.

12. The method according to claim 1, wherein the one or more reference movements of the input device and the one or more corresponding reference movements of the manipulator are recorded simultaneously or sequentially.

13. The method according to claim 1,
wherein one or more external operating elements are configured to switch between operating modes or to trigger an action of the tool; and
wherein an external monitor is configured to present images from a camera system.

14. A robot system comprising a control device, a manipulator and an input device,
wherein the control device is configured to allow an alignment of the manipulator with the input device by:
recording executed reference movements of the input device and corresponding reference movements of the manipulator respectively provided by position sensors of the input device and manipulator, the executed reference movements of the input device defining a reference coordinate system of the input device and the corresponding reference movements of the manipulator defining a reference coordinate system of the manipulator,
calculating a transformation matrix based on the recorded reference movements; and
using the calculated transformation matrix for the alignment of subsequent movements of the input device with corresponding movements of the manipulator.

15. The method according to claim 7, wherein the tool comprises a medical instrument.

16. The method according to claim 9, wherein the input device comprises a non-contact sensor selected from the group consisting of KINECT cameras and a LEAP MOTION devices.

17. The method according to claim 10, wherein the input device is detachably mounted.

18. The method according to claim 11, wherein the input device is detachably mounted.

19. The method according to claim 13, wherein the one or more external operating elements comprise a foot-operated switch connected to the control device.

20. The method according to claim 13, wherein the camera system comprises one or more of an endoscope camera, an external imaging system or navigation system.

* * * * *